(12) United States Patent
Ikeda

(10) Patent No.: US 10,078,053 B2
(45) Date of Patent: Sep. 18, 2018

(54) GAS CONCENTRATION ESTIMATION DEVICE

(71) Applicant: IMAGINEERING, Inc., Kobe-shi, Hyogo (JP)

(72) Inventor: Yuji Ikeda, Kobe (JP)

(73) Assignee: IMAGINEERING, INC., Kobe-shi (JP)

(*) Notice: Subject to any disclaimer, the term of this patent is extended or adjusted under 35 U.S.C. 154(b) by 133 days.

(21) Appl. No.: 14/369,020

(22) PCT Filed: Dec. 26, 2012

(86) PCT No.: PCT/JP2012/083607
§ 371 (c)(1),
(2) Date: Jun. 26, 2014

(87) PCT Pub. No.: WO2013/099923
PCT Pub. Date: Jul. 4, 2013

(65) Prior Publication Data
US 2015/0015881 A1 Jan. 15, 2015

(30) Foreign Application Priority Data
Dec. 28, 2011 (JP) .................. 2011-289568

(51) Int. Cl.
*G01N 21/68* (2006.01)
*G01N 21/67* (2006.01)
(Continued)

(52) U.S. Cl.
CPC ............. *G01N 21/68* (2013.01); *G01N 21/67* (2013.01); *G01N 33/0062* (2013.01);
(Continued)

(58) Field of Classification Search
CPC ......... G01N 1/2252; G01N 2021/8578; G01N 21/67; G01N 21/68; G01N 2201/067; G01N 33/004; G01N 33/0062
See application file for complete search history.

(56) References Cited

U.S. PATENT DOCUMENTS 4,066,904 A * 1/1978 Bertaux .................. G01N 21/33
250/372
4,902,099 A * 2/1990 Okamoto ............... G01N 21/73
219/121.36
(Continued)

FOREIGN PATENT DOCUMENTS

JP 09-304280 A 11/1997
JP 2008/059976 A 3/2008
(Continued)

OTHER PUBLICATIONS

Mitsuda, Yoshitaka, Ken-itsu Tanaka, and Toyonobu Yoshida. "Insitu emission and mass spectroscopic measurement of chemical species responsible for diamond growth in a microwave plasma jet." Journal of applied physics 67.8 (1990): 3604-3608.*
(Continued)

*Primary Examiner* — Tri Ton
*Assistant Examiner* — Rufus Phillips
(74) *Attorney, Agent, or Firm* — Westerman, Hattori, Daniels & Adrian, LLP

(57) ABSTRACT

The present invention aims at realizing a gas concentration estimation apparatus with versatility wherein the gas concentration estimation apparatus estimates concentration of a target component in an analyte gas by analyzing a light emitted from plasma of the analyte gas. The present invention is directed to a gas concentration estimation apparatus including: a plasma generation device that turns an analyte gas into a plasma state; and an analysis device that analyzes plasma light emitted from the plasma generated by the
(Continued)

plasma generation device and estimates concentration of a target component in the analyte gas wherein the analysis device estimates the concentration of the target component based on luminescence intensity of a wavelength component corresponding to luminescence from a predetermined radical within the plasma light, and the predetermined radical is different in atomic structure from the target component and includes an atom or a molecule separated from the target component.

10 Claims, 6 Drawing Sheets

(51) Int. Cl.
*G01N 33/00* (2006.01)
*G01N 1/22* (2006.01)
*G01N 21/85* (2006.01)

(52) U.S. Cl.
CPC ......... *G01N 1/2252* (2013.01); *G01N 33/004* (2013.01); *G01N 2021/8578* (2013.01); *G01N 2201/067* (2013.01)

(56) References Cited

U.S. PATENT DOCUMENTS

| | | | | |
|---|---|---|---|---|
| 5,184,501 | A * | 2/1993 | Lewis et al. | 73/23.31 |
| 5,986,757 | A * | 11/1999 | Seltzer | G01J 3/443 |
| | | | | 356/307 |
| 6,682,700 | B1 * | 1/2004 | Mills et al. | 422/98 |
| 7,701,578 | B1 * | 4/2010 | Herring | G01J 3/443 |
| | | | | 250/374 |
| 2004/0237505 | A1* | 12/2004 | Leipertz | F01N 1/00 |
| | | | | 60/274 |
| 2008/0055594 | A1* | 3/2008 | Hadidi | H05H 1/30 |
| | | | | 356/316 |
| 2009/0011147 | A1 | 1/2009 | Dictus | |
| 2009/0068768 | A1* | 3/2009 | Urbanowicz | G01N 21/631 |
| | | | | 438/9 |
| 2010/0055001 | A1* | 3/2010 | Ikeda | G01N 21/71 |
| | | | | 422/108 |
| 2010/0200390 | A1* | 8/2010 | Ikeda | B01D 53/32 |
| | | | | 204/157.15 |

FOREIGN PATENT DOCUMENTS

| | | |
|---|---|---|
| JP | 2009-065169 A | 3/2009 |
| JP | 2010-071271 A | 4/2010 |

OTHER PUBLICATIONS

Machala, Z., et al. "Emission spectroscopy of atmospheric pressure plasmas for bio-medical and environmental applications." Journal of Molecular Spectroscopy 243.2 (2007): 194-201.*
Ferioli, Francesco, and Steven G. Buckley. "Measurements of hydrocarbons using laser-induced breakdown spectroscopy." Combustion and Flame 144.3 (2006): 435-447.*
Kawahara, N., et al. "Fuel concentration measurement of premixed mixture using spark-induced breakdown spectroscopy." Spectrochimica Acta Part B: Atomic Spectroscopy 64.10 (2009): 1085-1092.*
Beduneau, J. L., et al. "Laser-induced radical generation and evolution to a self-sustaining flame." Combustion and Flame 156.3 (2009): 642-656.*
Ikeda, Yuji, Ahsa Moon, and Masashi Kaneko. "Development of microwave-enhanced spark-induced breakdown spectroscopy." Applied Optics 49.13 (2010): C95-C100.*
International Search Report dated May 14, 2013, issued in corresponding application No. PCT/JP2012/083607.
Lago, Viviana, et al., "Electron and vibrational temperatures in hypersonic CO2-N2 plasma jets", Plasma Sources Science and Technology, 2007, the United Kingdom, vol. 16, No. 1, pp. 139-148, cited in ISR.

* cited by examiner

GAS CONCENTRATION ESTIMATION
DEVICE

TECHNICAL FIELD

The present invention relates to a gas concentration estimation apparatus that estimates concentration of a target component in an analyte gas by analyzing alight emitted from plasma of the analyte gas, and a gas concentration estimation method.

BACKGROUND ART

Conventionally, there is known a gas concentration estimation apparatus that estimates concentration of a target component in an analyte gas by analyzing a light emitted from plasma of the analyte gas. For example, Japanese Unexamined Patent Application Publication No. 1997-304280 discloses a gas concentration estimation apparatus of this kind.

More particularly, Japanese Unexamined Patent Application Publication No. 1997-304280 discloses a concentration measuring method of carbon dioxide by means of the laser induced fluorescence method. The above described concentration measuring method causes a carbon dioxide molecule to absorb a plurality of photons at once in view of the fact that it is hard to acquire a laser capable of exciting a carbon dioxide molecule to a target energy level with absorption of one photon.

PRIOR ART DOCUMENTS

Patent Documents

Patent Document 1: Japanese Unexamined Patent Application Publication No. 1997-304280

THE DISCLOSURE OF THE INVENTION

Problems to be Solved by the Invention

However, the conventional gas concentration estimation apparatus requires a special photodetector for detecting the luminescence intensity of a wavelength component corresponding to luminescence of carbon dioxide assumed as the target component, thereby encountering a drawback of lacking versatility.

The present invention has been made in view of the above described problem, and it is an object of the present invention to realize a gas concentration estimation apparatus with versatility in the gas concentration estimation apparatus that estimates concentration of a target component in an analyte gas by analyzing a light emitted from plasma in the analyte gas.

Means for Solving the Problems

In accordance with a first aspect of the present invention, there is provided a gas concentration estimation apparatus, including: a plasma generation unit that turns an analyte gas into a plasma state; an analysis unit that estimates concentration of a target component in the analyte gas by analyzing plasma light emitted from the plasma generated by the plasma generation unit. The analysis unit is adapted to estimate the concentration of the target component based on luminescence intensity of a wavelength component corresponding to luminescence from a predetermined radical within the plasma light. The predetermined radical is different in atomic structure from the target component and includes an atom or a molecule separated from the target component.

According to the first aspect of the present invention, the concentration of the target component in the analyte gas is estimated by analyzing the plasma light emitted from the plasma of the analyte gas. The concentration of the target component is estimated based on the luminescence intensity of the wavelength component corresponding to the luminescence from the predetermined radical within the plasma light. The predetermined radical is intended to mean a predetermined radical different in atomic structure from the target component and includes an atom or a molecule separated from the target component. For example, in a case in which carbon dioxide is regarded as the target component, a CN radical including a carbon atom separated from the carbon dioxide molecule is employed as the predetermined radical.

In accordance with a second aspect of the present invention, in addition to the first aspect of the present invention, the analysis unit is adapted to estimate concentration of carbon dioxide as the target component based on luminescence intensity of a wavelength component corresponding to luminescence from the CN radical within the plasma light.

According to the second aspect of the present invention, the carbon dioxide concentration is estimated based on the luminescence intensity of the wavelength component corresponding to the luminescence from the CN radical within the plasma light, since, in a case in which the analyte gas includes carbon dioxide, the luminescence intensity of the luminescence from the CN radical included in the plasma light of the analyte gas correlates with the carbon dioxide concentration.

In accordance with a third aspect of the present invention, an exhaust gas emitted after combustion of hydrocarbon is regarded as the analyte gas and carbon dioxide in the analyte gas is regarded as the target component, and the analysis unit is adapted to estimate unburned hydrocarbon concentration in the exhaust gas, and to correct, based on the estimated unburned hydrocarbon concentration, the carbon dioxide concentration estimated based on the luminescence intensity of the wavelength component corresponding to the luminescence from the CN radical.

According to the third aspect of the present invention, using the estimation result of the unburned hydrocarbon concentration in the exhaust gas, the carbon dioxide concentration estimated based on the luminescence intensity of the wavelength component corresponding to the luminescence from the CN radical is corrected. In a case in which the exhaust gas includes unburned hydrocarbon, when the analyte gas is turned into the plasma state, a carbon atom separated from the hydrocarbon also produces the CN radical. Accordingly, there is a concern that an error with respect to an actual value should be included in the carbon dioxide concentration estimated merely from the luminescence intensity of the wavelength component corresponding to the luminescence from the CN radical. According to the third aspect of the present invention, the carbon dioxide concentration is corrected using the estimation result of the hydrocarbon concentration in order to reduce the error due to the unburned hydrocarbon.

In accordance with a fourth aspect of the present invention, in addition to the third aspect of the present invention, the analysis unit is adapted to estimate the unburned hydrocarbon concentration based on the luminescence intensity of the wavelength component corresponding to the luminescence from CH radical within the plasma light.

According to the fourth aspect of the present invention, the unburned hydrocarbon concentration is estimated based on the luminescence intensity of the wavelength component corresponding to the luminescence from the CH radical.

In accordance with a fifth aspect of the present invention, in addition to any one of the second to fourth aspects of the present invention, the analysis unit is adapted to estimate the carbon dioxide concentration from the luminescence intensity of the wavelength component corresponding to the luminescence from the CN radical based on a calibration curve indicative of relationship between the carbon dioxide concentration and the luminescence intensity of the wavelength component corresponding to the luminescence from the CN radical.

According to the fifth aspect of the present invention, the carbon dioxide concentration is estimated from the luminescence intensity of the wavelength component corresponding to the luminescence from the CN radical by using the calibration curve indicative of the relationship between the carbon dioxide concentration and the luminescence intensity of the wavelength component corresponding to the luminescence from the CN radical.

In accordance with a sixth aspect of the present invention, in addition to the first aspect of the present invention, the analysis unit is adapted to estimate concentration of water vapor as the target component based on the luminescence intensity of the wavelength component corresponding to the luminescence from OH radical within the plasma light.

According to the sixth aspect of the present invention, the water vapor concentration is estimated based on the luminescence intensity of the wavelength component corresponding to the luminescence from the OH radical, since, in a case in which the analyte gas includes water vapor, the luminescence intensity of the luminescence from the OH radical included in the plasma light of the analyte gas correlates with the water vapor concentration.

In accordance with a seventh aspect of the present invention, in addition to any one of the first to sixth aspects of the present invention, the gas concentration estimation apparatus further includes a flow rate detection unit that detects flow rate of the analyte gas flowing into a plasma region in which the plasma generation unit generates the plasma, and the analysis unit is adapted to correct, based on the flow rate detected by the flow rate detection unit, the concentration of the target component estimated based on the luminescence intensity of the wavelength component corresponding to the luminescence from the predetermined radical.

According to the seventh aspect of the present invention, the flow rate detection unit detects the flow rate of the analyte gas flowing into the plasma region. In a case in which the plasma is generated at a location where the gas flows, the luminescence intensity of the plasma light changes depending on the flow rate. Accordingly, there is a concern that an error should be included in the value of the concentration of the target component estimated based on the luminescence intensity of the wavelength component corresponding to the luminescence from the predetermined radical unless the flow rate is considered. In order to solve the above described problem, according to the seventh aspect of the present invention, the concentration of the target component estimated based on the luminescence intensity of the wavelength component corresponding to the luminescence from the predetermined radical is corrected using the flow rate detected by the flow rate detection unit.

In accordance with an eighth aspect of the present invention, in addition to any one of the first to seventh aspects of the present invention, the gas concentration estimation apparatus further includes a shield member provided upstream of a plasma region in which the plasma generation unit generates the plasma with respect to a flowing direction of the analyte gas, and adapted to partially shield the plasma region.

According to the eighth aspect of the present invention, the shield member for partially shielding the plasma region is arranged upstream of the plasma region. Accordingly, the plasma light is prevented from changing in luminescence intensity under the influence of the flow.

In accordance with a ninth aspect of the present invention, in addition to the eighth aspect of the present invention, the analysis unit is adapted to analyze the plasma light extracted from a region not shielded by the shield member within the plasma region, and to estimate the concentration of the target component in the analyte gas.

According to the ninth aspect of the present invention, the concentration of the target component in the analyte gas is estimated by analyzing the plasma light extracted from a region not shielded by the shield member (hereinafter, referred to as a "non-shielded region") within the plasma region. In a case in which a time series variation of the concentration of the target component is to be estimated at a location where the gas flows, the variation of the concentration in the region shielded by the shield member will not sufficiently follow the variation of the concentration of the bulk flow. According to the ninth aspect of the present invention, the plasma light of the non-shielded region is extracted in order to estimate the concentration of the target component since the shield member suppresses the influence of the flow to some extent and the variation of the concentration in the non-shielded region follows the variation of the concentration of the bulk flow to some extent.

In accordance with a tenth aspect of the present invention, there is provided a gas concentration estimation method including: plasma generation step of turning an analyte gas into a plasma state; and an analysis step of analyzing a plasma light emitted from plasma generated in the plasma generation step, and estimating concentration of a target component in the analyte gas. In the analysis step, the concentration of the target component is estimated based on luminescence intensity of a wavelength component corresponding to luminescence from a predetermined radical within the plasma light. The predetermined radical is different in atomic structure from the target component and includes an atom or a molecule separated from the target component.

According to the tenth aspect of the present invention, similarly to the first aspect of the present invention, the concentration of the target component is estimated based on the luminescence intensity of the wavelength component corresponding to the luminescence from a predetermined radical within the plasma light. The predetermined radical is different in atomic structure from the target component and includes an atom or a molecule separated from the target component.

Effect of the Invention

According to the present invention, the concentration of the target component is estimated based on the luminescence intensity of the wavelength component corresponding to the luminescence, not from the target component, but from the predetermined radical different in atomic structure from the target component and including an atom or a molecule separated from the target component. Accordingly, for example, in a case in which carbon dioxide is regarded as the target component, it is possible to employ a general purpose photodetector in order to detect the luminescence intensity of the wavelength component corresponding to the luminescence from the CN radical. Therefore, it is possible to realize a gas concentration estimation apparatus with versatility.

Furthermore, according to the third aspect of the present invention, the carbon dioxide concentration estimated based on the luminescence intensity of the wavelength component corresponding to the luminescence from the CN radical is corrected using the estimation result of the hydrocarbon concentration for the purpose of reducing the error due to unburned hydrocarbon. Accordingly, it is possible to improve estimation accuracy of the carbon dioxide concentration in the exhaust gas that includes hydrocarbon.

Furthermore, according to the seventh aspect of the present invention, since the luminescence intensity of the plasma light changes depending on the flow rate of the analyte gas, the concentration of the target component estimated based on the luminescence intensity of the wavelength component corresponding to the luminescence from the predetermined radical is corrected using the detected flow rate of the analyte gas. Accordingly, it is possible to improve estimation accuracy of the concentration of the target component at a location where the gas flows.

Furthermore, according to the eighth aspect of the present invention, since the shield member that partially shields the plasma region is provided upstream of the plasma region, the luminescence intensity of the plasma light is prevented from changing under the influence of the flow. Accordingly, it is possible to improve estimation accuracy of the concentration of the target component at a location where the gas flows.

BEST MODE FOR CARRYING OUT THE INVENTION

In the following, a description will be given of an embodiment of the present invention with reference to the accompanying drawings. It should be noted that the following embodiments are merely preferable examples, and do not limit the scope of the present invention, applied field thereof, or application thereof.

Figure 1:
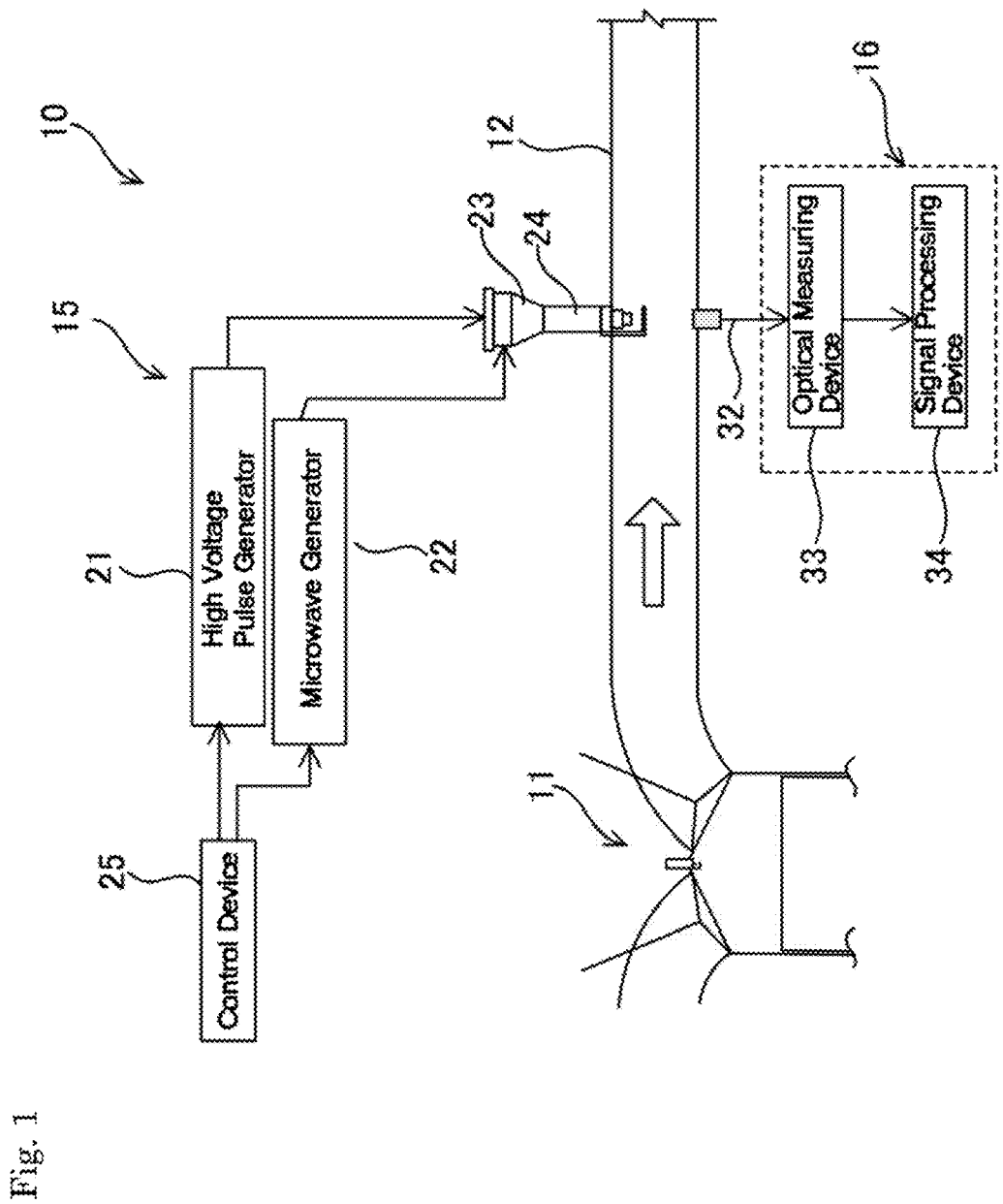
FIG. 1 is a schematic configuration diagram of a gas concentration estimation apparatus according to an embodiment.
Figure 2:
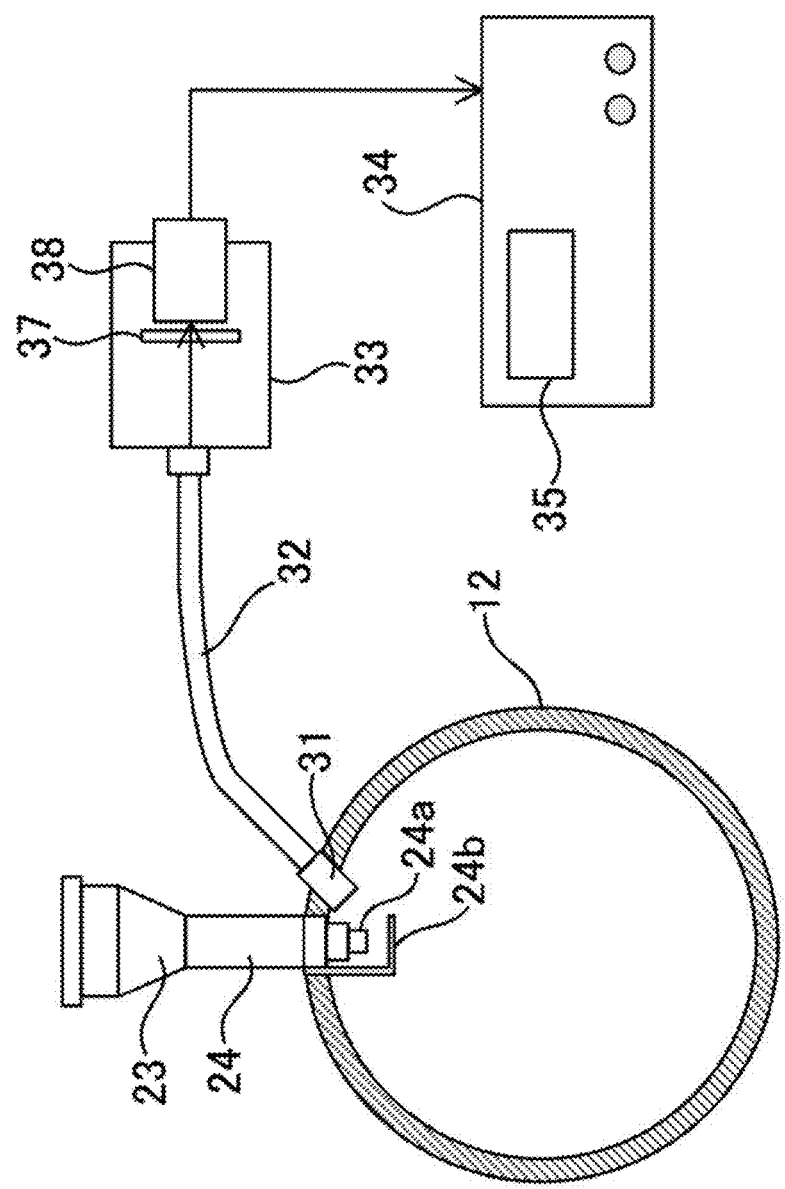
FIG. 2 is a schematic configuration diagram of a main part of the gas concentration estimation apparatus according to the embodiment.

The present embodiment is directed to a gas concentration estimation apparatus 10 for estimating carbon dioxide concentration wherein an exhaust gas from an engine 11 is regarded as an analyte gas and carbon dioxide in the analyte gas is regarded as a target component. As shown in FIGS. 1 and 2, the gas concentration estimation apparatus 10 is attached to an exhaust pipe 12 of the engine 11. The gas concentration estimation apparatus 10 is adapted to measure the carbon dioxide concentration in the exhaust gas flowing through the exhaust pipe 12.

The gas concentration estimation apparatus 10 is provided with a plasma generation device 15 and an analysis device 16. The plasma generation device 15 constitutes a plasma generation unit that turns the analyte gas into a plasma state. The analysis device 16 constitutes an analysis unit that is adapted to analyze plasma light emitted from plasma generated by the plasma generation device 15 and to estimate the carbon dioxide concentration in the analyte gas.

Plasma Generation Device

The plasma generation device 15 is provided with a high voltage pulse generator 21, a microwave generator 22, a mixer 23, a discharger 24, and a control device 25. The control device 25 is adapted to control the high voltage pulse generator 21 and the microwave generator 22.

The high voltage pulse generator 21, upon receiving a discharge signal from the control device 25, boosts a voltage applied from a direct current power supply (not shown), and generates a boosted high voltage pulse. The high voltage pulse generator 21 outputs the high voltage pulse to the mixer 23. The high voltage pulse is an impulse-like voltage signal having a peak voltage of 6 kV to 40 kV, for example.

Figure 3:
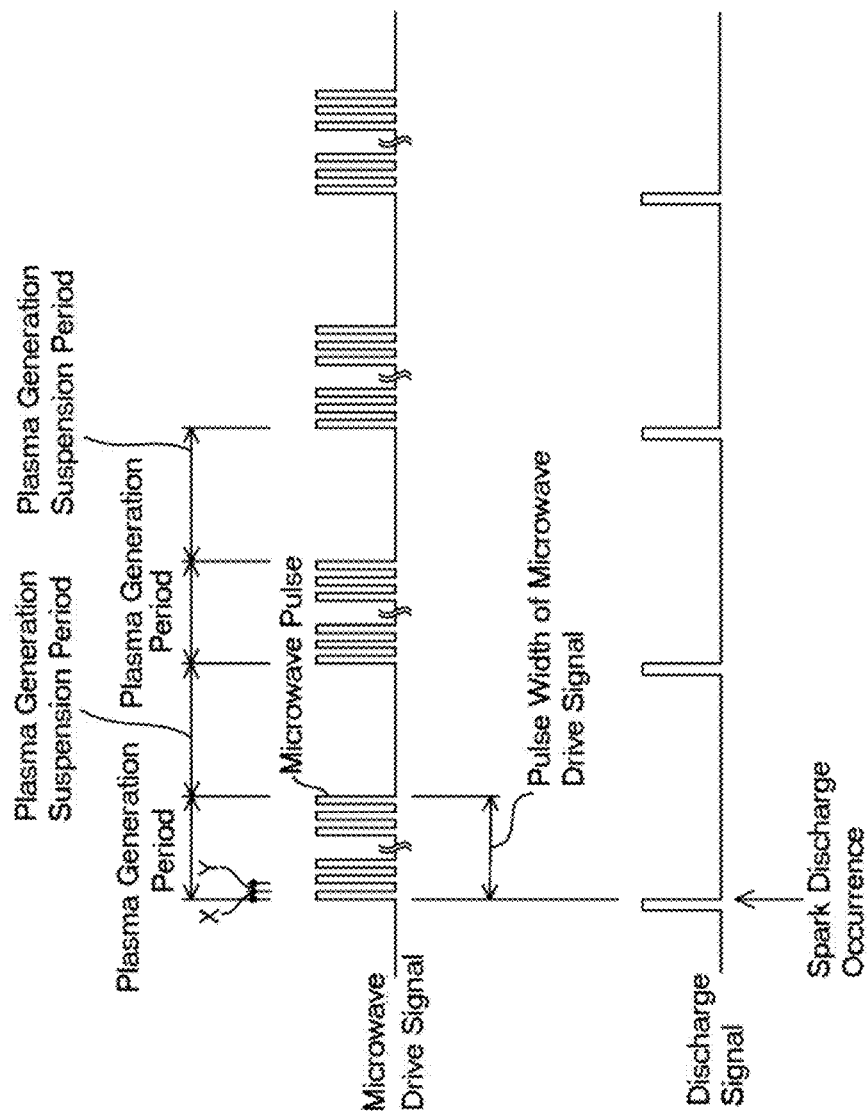
FIG. 3 is a time chart of a discharge signal and a microwave drive signal according to the embodiment.

The microwave generator 22, upon receiving a microwave drive signal from the control device 25, generates a microwave pulse using power supplied from a direct current power supply (not shown). As shown in FIG. 3, the microwave generator 22 repeatedly outputs the microwave pulse at a predetermined duty cycle during a period from the rise to the fall of the microwave drive signal (a period of a pulse width of the microwave drive signal). The microwave generator 22 repeatedly outputs the microwave pulse to the mixer 23.

Although, in the microwave generator 22 according to the present embodiment, a semiconductor oscillator generates the microwave pulse, other types of oscillators such as a magnetron may be employed in place of the semiconductor oscillator.

The mixer 23 receives the high voltage pulse and the microwave pulse at different input terminals, and outputs the high voltage pulse and the microwave pulse to the discharger 24 from a same output terminal. The mixer 23 is configured to be able to mix the high voltage pulse and the microwave pulse.

The discharger 24 is an ignition plug 24, for example. The ignition plug 24 is integrated with the mixer 23. The ignition plug 24 is attached to the exhaust pipe 12 so that a discharge gap between a central electrode 24a and a ground electrode 24b should locate within the exhaust pipe 12. In the ignition plug 24, an input terminal electrically connected to the central electrode 24a is electrically connected to the output terminal of the mixer 23, though not illustrated.

The plasma generation device 15 performs a plasma generation operation of generating microwave plasma. The plasma generation operation is started when the control device 25 outputs the discharge signal and the microwave drive signal. As described above, the high voltage pulse generator 21 outputs the high voltage pulse upon receiving the discharge signal, and the microwave generator 22 outputs the microwave pulse upon receiving the microwave drive signal. The high voltage pulse and the microwave pulse are supplied to the central electrode 24a of the ignition plug 24 via the mixer 23.

In the ignition plug 24, a spark discharge is caused to occur at the discharge gap owing to the high voltage pulse. Furthermore, the discharge plasma generated by the spark discharge is irradiated with the microwave pulse from the central electrode 24a. As a result of this, the discharge plasma absorbs the microwave energy and expands, thereby generating comparatively large microwave plasma. In a plasma region in which the microwave plasma is generated, the exhaust gas flowing through the exhaust pipe 12 is turned into the plasma state.

Although, according to the present embodiment, the central electrode 24a functions as an emission antenna, the emission antenna may be arranged adjacently to the central electrode 24a. In this case, the microwave pulse is supplied to the emission antenna via a path other than that of the high voltage pulse.

The microwave drive signal is a pulse signal having a width of several milliseconds, for example. The microwave generator 22 repeatedly outputs the microwave pulses at the predetermined duty cycle during the period of the pulse width of the microwave drive signal. During this period, as shown in FIG. 3, an on-period X (X being several microseconds) in which the microwave pulse is outputted and an off-period Y (Y being several microseconds) in which the microwave pulse is not outputted are repeated. At the central electrode 24a of the ignition plug 24, radiation and non-radiation of the microwave pulse are repeated at the duty cycle. As a result of this, the microwave plasma is maintained in a state of non-equilibrium plasma without being turned into thermal plasma.

It is to be noted that if the off-period Y in which the microwave pulse is not outputted is set too long, the microwave plasma will be extinguished. Therefore, the length of the off-period Y is configured so that the microwave plasma should not be extinguished before the subsequent microwave pulse is radiated. During the plasma generation operation, the microwave plasma is maintained over the time period (period in which the microwave pulses are repeatedly outputted) of the pulse width of the microwave drive signal. This time period constitutes a plasma generation period.

The plasma generation device 15 repeatedly performs the plasma generation operation with interval of several milliseconds, which will be referred to as a "plasma generation stop period". At the discharge gap, a plasma generation state in which the microwave plasma is generated and a plasma extinction state in which the microwave plasma is extinguished are repeated. The plasma generation period and the plasma generation stop period are repeated at a short cycle.

Analysis Device

The analysis device 16 performs an analysis operation of analyzing the plasma light of the microwave plasma generated by the plasma generation operation. The analysis device 16 performs the analysis operation in synchronization with the plasma generation operation which is repeated at the short cycle.

As shown in FIGS. 1 and 2, the analysis device 16 is provided with an optical fiber 32, an optical measuring device 33, and a signal processing device 34. In the analysis device 16, the optical measuring device 33 acquires the plasma light of the microwave plasma via the optical fiber 32. The optical measuring device 33 extracts a wavelength component (388 nm) corresponding to luminescence from the CN radical, photoelectric-converts the extracted wavelength component into an electric signal, and outputs the converted electric signal. The signal processing device 34 estimates the carbon dioxide concentration using the electric signal outputted from the optical measuring device 33. As shown in FIG. 2, the signal processing device 34 is provided with a monitor 35 that displays the carbon dioxide concentration estimated by the signal processing device 34.

More particularly, the optical fiber 32 is mounted to the exhaust pipe 12 via a mounting member 31. The optical fiber 32 is mounted so that one end surface (hereinafter, referred to as an "incident surface") thereof should face toward the discharge gap, which is to be the plasma region. The other end of the optical fiber 32 is connected to the optical measuring device 33.

The optical measuring device 33 is provided with an optical filter 37 and a photodetector 38. The optical filter 37 is arranged at a location which the plasma light emitted from an emission surface of the optical fiber 32 passes through. The optical filter 37 allows the wavelength component corresponding to the luminescence from the CN radical to pass therethrough, from within the plasma light emitted thereto. The photodetector 38 is, for example, a PMT (PhotoMultiplier Tube). The photodetector 38 receives the light passing through the optical filter 37. The photodetector 38 receives the wavelength component corresponding to the luminescence from the CN radical. The photodetector 38 outputs to the signal processing device 34 the electric signal indicative of a voltage value corresponding to the intensity of the received wavelength component, i.e., the luminescence intensity of the wavelength component corresponding to the luminescence from the CN radical. As the photodetector 38, an instrument other than the photomultiplier tube may be employed as long as the time responsiveness is high.

The signal processing device 34 stores data of a calibration curve (see FIG. 4) indicative of relationship between the carbon dioxide concentration and the luminescence intensity of the wavelength component corresponding to the luminescence from the CN radical. The luminescence intensity of the wavelength component corresponding to the luminescence from the CN radical (more particularly, the voltage value of the electric signal indicative of the luminescence intensity of the wavelength component corresponding to the luminescence from the CN radical) is measured in advance by means of a predetermined experimental device by gradually changing the carbon dioxide concentration contained in a gas which does not include any carbonaceous gas components other than the carbon dioxide. Based on this measurement result, the data of the calibration curve is prepared. The data of the calibration curve shows the carbon dioxide concentrations in one-to-one relationship with the voltage values of the electric signals each indicative of the luminescence intensity of the wavelength component corresponding to the luminescence from the CN radical.

The signal processing device 34 reads a value of the carbon dioxide concentration corresponding to the voltage value of the electric signal outputted from the photodetector 38 based on the data of the calibration curve. The signal processing device 34 outputs the read value of the carbon dioxide concentration to the monitor 35.

Operation of Gas Concentration Estimation Apparatus

The gas concentration estimation apparatus 10 repeatedly performs a plasma generation step and an analysis step while the engine 11 is operating.

In the plasma generation step, the plasma generation device 15 generates and maintains for several milliseconds the microwave plasma at the discharge gap. The exhaust gas, which serves as the analyte gas, is turned into the plasma state.

In the analysis step, the analysis device 16 analyzes the plasma light emitted from the microwave plasma generated in the plasma generation step, and estimates the carbon dioxide concentration in the exhaust gas. The analysis step is performed for each repeated plasma generation step.

In the analysis step, the wavelength component corresponding to the luminescence from the CN radical is extracted by the optical filter 37 from the plasma light of the microwave plasma acquired by the optical measuring device 33, and the electric signal indicative of the luminescence intensity of the wavelength component corresponding to the luminescence from the CN radical is generated by the photodetector 38. Then, the electric signal indicative of the luminescence intensity of the wavelength component corresponding to the luminescence from the CN radical is inputted into the signal processing device 34. The value of the carbon dioxide concentration corresponding to the voltage value of the electric signal is read from the data of the calibration curve. In the signal processing device 34, the analysis step is performed for each plasma generation step, and the carbon dioxide concentration is estimated at the short cycle. As a result of this, time series data with high temporal resolution is created with respect to the carbon dioxide concentration.

Effect of Embodiment

According to the embodiment, the carbon dioxide concentration is estimated based on the luminescence intensity of the wavelength component corresponding to the luminescence not from the carbon dioxide but from the CN radical wherein the CN radical is different in atomic structure than the carbon dioxide and includes an atom or a molecule separated from the carbon dioxide. Accordingly, since a general purpose photodetector can be employed to detect the luminescence intensity of the wavelength component corresponding to the luminescence from the CN radical, it is possible to realize a gas concentration estimation apparatus 10 with versatility.

First Modified Example of Embodiment

Figure 4:
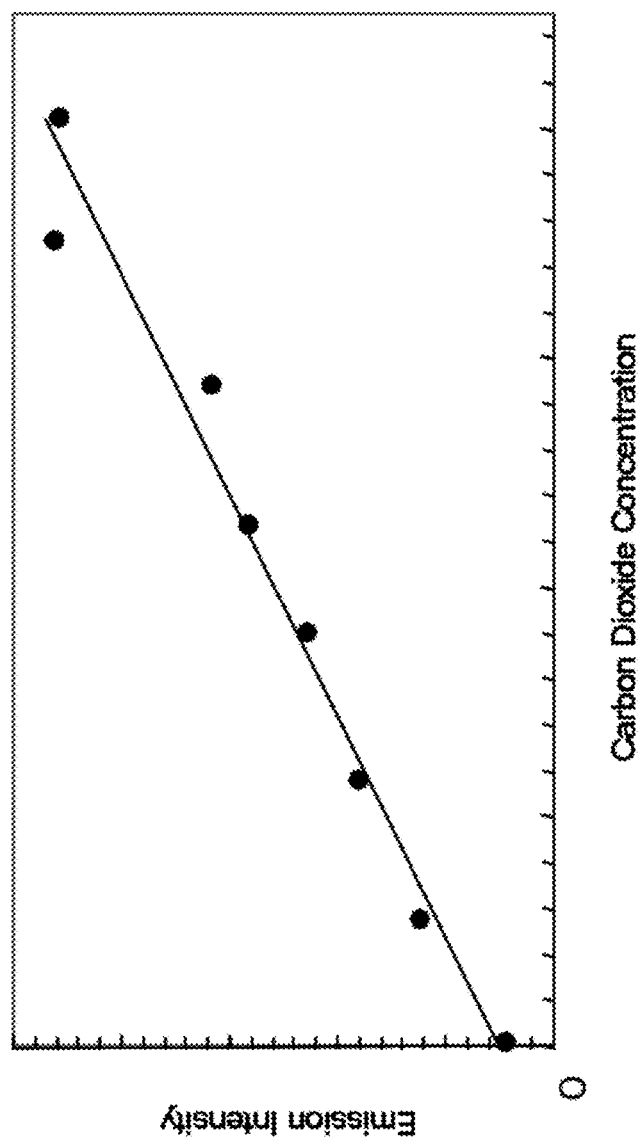
FIG. 4 is a diagram of a calibration curve indicative of relationship between carbon dioxide concentration and luminescence intensity of a wavelength component corresponding to luminescence from a CN radical.

According to the first modified example, the analysis device 16 estimates the unburned hydrocarbon concentration in the exhaust gas, and, using the estimation result, corrects the value of the carbon dioxide concentration which has been estimated based on the luminescence intensity of the wavelength component corresponding to the luminescence from the CN radical (the value of the carbon dioxide concentration which has been read from the data of the calibration curve shown in FIG. 4).

Figure 5:
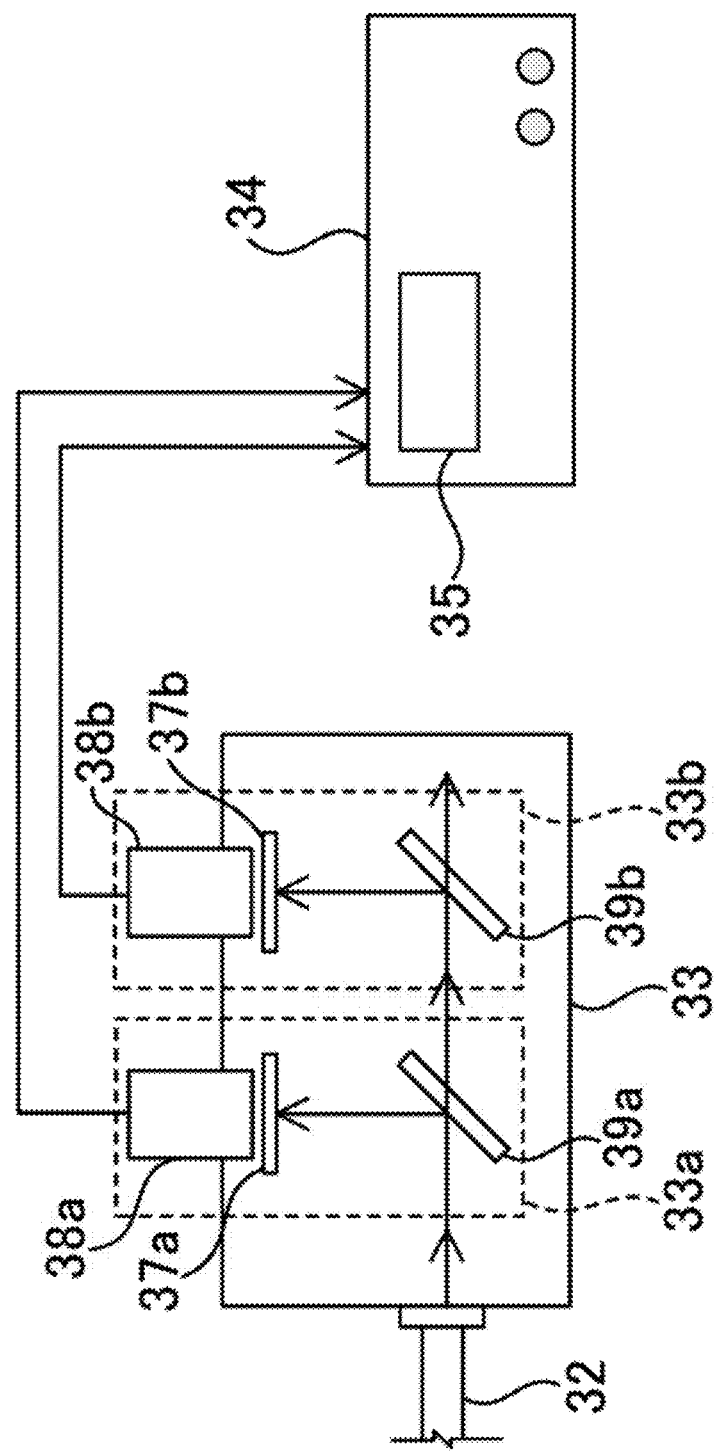
FIG. 5 is a schematic configuration diagram of an optical measuring device (spectroscope) according to a first modified example of the embodiment.

In the analysis device 16, as shown in FIG. 5, the optical measuring device 33 is constituted by a spectroscope 33 that disperses the plasma light acquired via the optical fiber 32. The optical measuring device 33 is provided with a first measuring part 33a that photoelectric-converts the wavelength component corresponding to the luminescence from the CN radical from the plasma light into a first electric signal and outputs the first electric signal, and a second measuring part 33b that photoelectric-converts the wavelength component corresponding to the luminescence from the CH radical into a second electric signal and outputs the second electric signal.

Each of the measuring parts 33a and 33b is provided with a dichroic mirror 39a or 39b, an optical filter 37a or 37b, and a photodetector 38a or 38b. The dichroic mirror 39a or 39b separates the plasma light. The optical filter 37a or 37b functions as an interference filter. The photodetector 38a or 38b is a photomultiplier tube, similarly to the embodiment.

The signal processing device 34 stores, in addition to the data of the calibration curve shown in FIG. 4 (hereinafter, referred to as "first data"), data of a calibration curve for estimating hydrocarbon concentration (hereinafter, referred to as "second data"). The second data is indicative of relationship between the hydrocarbon concentration and luminescence intensity of a wavelength component corresponding to luminescence from the CH radical. The luminescence intensity of the wavelength component corresponding to the luminescence from the CH radical is measured in advance by means of a predetermined experimental device by gradually changing the hydrocarbon concentration contained in a gas which does not include any carbonaceous gas components other than the hydrocarbon. Based on this measurement result, the data of the calibration curve is prepared. The second data shows the hydrocarbon concentrations in one-to-one relationship with the voltage values of the electric signals each indicative of the luminescence intensity of the wavelength component corresponding to the luminescence from the CH radical.

The signal processing device 34 reads from the first data a value of the carbon dioxide concentration (hereinafter, referred to as a "first read concentration") corresponding to the voltage value of the first electric signal. Also, the signal processing device 34 reads from the second data a value of the hydrocarbon concentration (hereinafter, referred to as a "second read concentration") corresponding to the voltage value of the second electric signal. The signal processing device 34 does not output the first read concentration as the final estimate value of the carbon dioxide concentration. The signal processing device 34 outputs, for example, a value acquired by subtracting the second read concentration from the first read concentration as the final estimate value of the carbon dioxide concentration.

Here, it is to be noted that the hydrocarbon concentration may be estimated by any other method such as a total hydrocarbon meter (total organic carbon meter) or the like.

Second Modified Example of Embodiment

According to the second modified example, the gas concentration estimation apparatus 10 estimates concentration of water vapor wherein the water vapor in the analyte gas is regarded as the target component.

The optical measuring device 33 extracts from the plasma light of the microwave plasma a wavelength component corresponding to luminescence from OH radical, photoelectric-converts the extracted wavelength component into an electric signal, and outputs the electric signal. A voltage value of the electric signal represents luminescence intensity of the wavelength component corresponding to the luminescence from the OH radical.

The signal processing device 34 estimates the water vapor concentration based on the electric signal outputted from the optical measuring device 33. Here, the water vapor concentration is estimated using data of a calibration curve indicative of relationship between the water vapor concentration and the luminescence intensity of the wavelength component corresponding to the luminescence from the OH radical. The signal processing device 34 estimates the water vapor concentration based on the luminescence intensity of the wavelength component corresponding to the luminescence from the OH radical.

Third Modified Example of Embodiment

Figure 6:
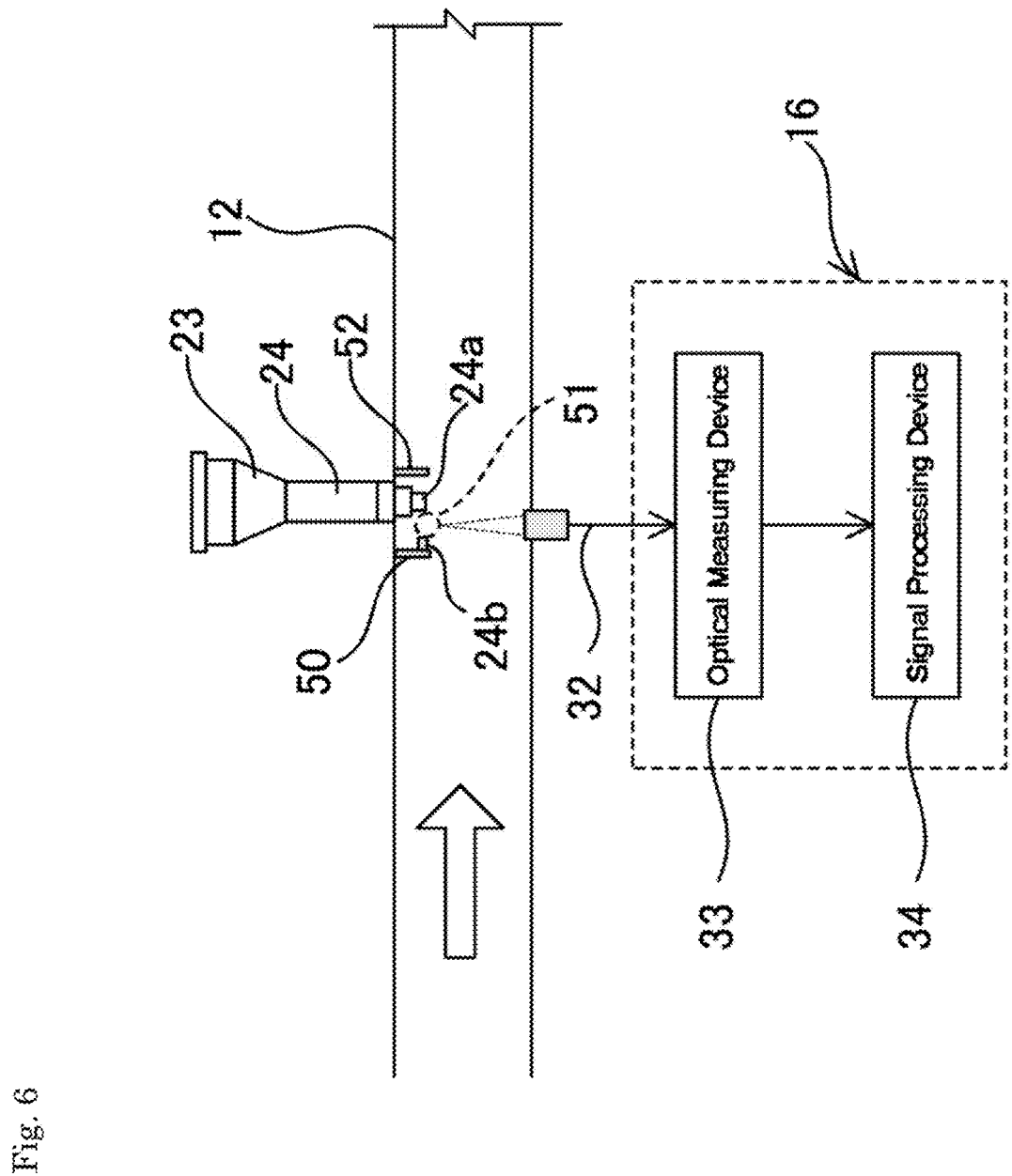
FIG. 6 is a schematic configuration diagram of a main part of a gas concentration estimation apparatus according to a third modified example of the embodiment.

According to the third modified example, as shown in FIG. 6, upstream of a plasma region 51 in which the plasma generation device 15 generates microwave plasma 51, a shield member 50 is provided for partially shielding the plasma region 51. The shield member 50 is an electrically conductive member in a plate-like shape protruded from an inner surface of the exhaust pipe 12. The shield member 50 is provided adjacently to a tip end part of the ignition plug 24. The shield member 50 is provided with the ground electrode 24b of the ignition plug 24. The ground electrode 24b is grounded via the shield member 50.

A plate-like member 52 is provided also downstream of the ignition plug 24 in the same shape as the shield member 50. By providing the plate-like member 52, the flow between the shield member 50 and the plate-like member 52 is stabilized.

The microwave plasma 51 is generated in a region on a side of the central electrode 24a between the ground electrode 24b and the central electrode 24a. The microwave plasma 51 partially protrudes from a tip end of the shield member 50 toward a side of a central axis of the exhaust pipe 12.

According to the third modified example, the analysis device 16 analyzes the plasma light extracted from a non-shielded region which is not shielded by the shield member 50 within the plasma region 51, and estimates the concentration of the target component in the analyte gas. More particularly, a light collecting optical system having a focal point located in the non-shielded region is provided on the optical fiber 32 on the side of the exhaust pipe 12, thereby extracting the plasma light of the non-shielded region. According to the third modified example, the plasma light is extracted to estimate the concentration of the target component from the non-shielded region where the influence of the flow is suppressed to some extent and the concentration varies in accordance with the variation of the concentration the bulk flow to some extent.

An upstream side surface of the shield member 50 may be slanted in order to reduce turbulence of the flow in the plasma region. In this case, the thickness of the shield member 50 increases toward the exhaust pipe 12.

Fourth Modified Example of Embodiment

According to the fourth modified example, the analysis device 16 is adapted to correct the value of the carbon dioxide concentration estimated based on the luminescence intensity of the wavelength component corresponding to the luminescence from the CN radical based on the flow rate of the analyte gas flowing into the plasma region in which the plasma generation device 15 generates the plasma. The flow rate of the analyte gas is detected by means of a flow rate detection device (a flow rate detection unit) arranged upstream of the ignition plug 24 in the exhaust pipe 12. Here, it is preferable to create data of a plurality of calibration curves in accordance with different flow rates of the analyte gas flowing into the plasma region, and select the data of the calibration curve to be used in accordance with the detection result of the flow rate detection device.

Other Embodiments

The embodiments described above may also be configured as follows.

In the embodiments described above, the plasma generation device 15 may generate the plasma by collecting laser light, and the plasma generation device 15 may generate the microwave plasma by supplying microwave energy to the plasma generated by collecting the laser light. In these cases, the laser induced fluorescence method may be employed to estimate the carbon dioxide concentration based on the luminescence intensity of the wavelength component corresponding to the luminescence from the CN radical.

Furthermore, in the embodiments described above, the plasma generation device 15 may generate the microwave plasma by supplying microwave energy to thermal electrons emitted from a thermal electron emitter such as a glow plug.

Furthermore, in the embodiments described above, plasma generated without using microwave may be employed to turn the analyte gas into the plasma state.

Furthermore, although, in the embodiments described above, the exhaust gas has been defined as the analyte gas, any other types of gas such as human expired breath may be used as the analyte gas.

INDUSTRIAL APPLICABILITY

The present invention is useful in relation to a gas concentration estimation apparatus that estimates concentration of a target component in an analyte gas by analyzing a light emitted from plasma of the analyte gas, and a gas concentration estimation method.

EXPLANATION OF REFERENCE NUMERALS

10 Gas Concentration Estimation Apparatus
11 Engine
12 Exhaust Pipe
15 Plasma Generation Device (Plasma Generation Unit)
16 Analysis Device (Analysis Unit)
23 Mixer
24 Discharger
32 Optical Fiber

What is claimed is:

1. A gas concentration estimation apparatus, comprising:
an exhaust pipe of an engine, an exhaust gas flowing from the engine into the exhaust pipe;
a plasma generation unit provided to the exhaust pipe and configured to turn the exhaust gas into a plasma state in the exhaust pipe;
an analysis unit that estimates concentration of a target component in the exhaust gas by analyzing plasma light emitted from the plasma generated by the plasma generation unit, wherein
the analysis unit is adapted to estimate the concentration of the target component based on luminescence intensity of a wavelength component corresponding to luminescence from a predetermined radical within the plasma light, the predetermined radical being different in atomic structure from the target component and including an atom or a molecule separated from the target component, an exhaust gas emitted after combustion of hydrocarbon is regarded as the exhaust gas and carbon dioxide in the exhaust gas is regarded as the target component, and the analysis unit is adapted to estimate unburned hydrocarbon concentration in the exhaust gas, and to correct, using the estimated unburned hydrocarbon concentration, the carbon dioxide concentration estimated based on the luminescence intensity of the wavelength component corresponding to the luminescence from the CN radical.

2. The gas concentration estimation apparatus according to claim 1, wherein the analysis unit is adapted to estimate concentration of carbon dioxide as the target component based on luminescence intensity of a wavelength component corresponding to luminescence from the CN radical within the plasma light.

3. The gas concentration estimation apparatus according to claim 1, wherein the analysis unit is adapted to estimate the unburned hydrocarbon concentration based on the luminescence intensity of the wavelength component corresponding to the luminescence from CH radical within the plasma light.

4. The gas concentration estimation apparatus according to claim 2, wherein the analysis unit is adapted to estimate the carbon dioxide concentration from the luminescence intensity of the wavelength component corresponding to the luminescence from the CN radical based on a calibration curve indicative of relationship between the carbon dioxide concentration and the luminescence intensity of the wavelength component corresponding to the luminescence from the CN radical.

5. The gas concentration estimation apparatus according to claim 1, wherein the analysis unit is adapted to estimate concentration of water vapor as the target component based on the luminescence intensity of the wavelength component corresponding to the luminescence from OH radical within the plasma light.

6. The gas concentration estimation apparatus according to claim 1, wherein the gas concentration estimation apparatus is further configured to detect a flow rate of the exhaust gas flowing into a plasma region in which the plasma generation unit generates the plasma, and the analysis unit is adapted to correct, based on the flow rate detected by the gas concentration estimation apparatus, the concentration of the target component estimated based on the luminescence intensity of the wavelength component corresponding to the luminescence from the predetermined radical.

7. The gas concentration estimation apparatus according to claim 1, wherein the gas concentration estimation apparatus further includes a shield member provided upstream of a plasma region in which the plasma generation unit generates the plasma with respect to a flowing direction of the exhaust gas, and adapted to partially shield the plasma region.

8. The gas concentration estimation apparatus according to claim 7, wherein the analysis unit is adapted to analyze the plasma light extracted from a region not shielded by the shield member within the plasma region, and to estimate the concentration of the target component in the exhaust gas.

9. The gas concentration estimation apparatus according to claim 1, wherein the plasma generation unit comprises a high voltage pulse generator and a microwave generator.

10. A gas concentration estimation method, comprising:

a step of generating an exhaust gas in an engine, the exhaust gas flowing from the engine into an exhaust pipe of the engine;

a plasma generation step of turning the exhaust gas into a plasma state in the exhaust pipe; and an analysis step of analyzing a plasma light emitted from plasma generated in the plasma generation step, and estimating concentration of a target component in the exhaust gas, wherein in the analysis step, the concentration of the target component is estimated based on luminescence intensity of a wavelength component corresponding to luminescence from a predetermined radical within the plasma light, the predetermined radical being different in atomic structure from the target component and including an atom or a molecule separated from the target component, an exhaust gas emitted after combustion of hydrocarbon is regarded as the exhaust gas and carbon dioxide in the exhaust gas is regarded as the target component, and the analysis step comprises estimating unburned hydrocarbon concentration in the exhaust gas and correcting, using the estimated unburned hydrocarbon concentration, the carbon dioxide concentration estimated based on the luminescence intensity of the wavelength component corresponding to the luminescence from the CN radical.

* * * * *